United States Patent [19]

Barber et al.

[11] Patent Number: 4,649,747

[45] Date of Patent: Mar. 17, 1987

[54] COOLANT LINE HYDROMETER

[76] Inventors: Michael D. Barber, 10169 Sunny Dr., Covington, Ga. 30209; William G. Kipp, 1219 Lakeview Dr., Apt. 6, Conyers, Ga. 30207

[21] Appl. No.: 699,330

[22] Filed: Feb. 7, 1985

[51] Int. Cl.$^4$ ............................................. G01N 9/10
[52] U.S. Cl. .................................................... 73/440
[58] Field of Search .................. 73/440, 441, 444–448, 73/450–452, 454, 431

[56] References Cited

U.S. PATENT DOCUMENTS

| | | | |
|---|---|---|---|
| 1,683,735 | 9/1928 | Smith | 73/444 |
| 2,681,034 | 6/1954 | Mannion | 73/431 |
| 3,460,395 | 8/1969 | Shaw | 73/444 |
| 3,626,763 | 12/1971 | White | 73/440 |
| 3,631,727 | 1/1972 | White | 73/440 |
| 3,641,825 | 2/1972 | Reid | 73/444 |
| 3,895,964 | 7/1975 | Sakamoto | 73/447 |

Primary Examiner—Jerry W. Myracle
Assistant Examiner—Robert R. Raevis
Attorney, Agent, or Firm—Newton, Hopkins & Ormsby

[57] ABSTRACT

A hydrometer unit permanently connected in an engine coolant line enables an immediate visual check on the adequacy of the anti-freeze constituent, such as ethylene glycol, in the system. The hydrometer includes a coolant receiving chamber having a transparent viewing portion and a number of variously colored float elements within the chamber provide an accurate indication of anti-freeze strength based on specific gravity. No manipulation of the hydrometer is required to enable a checking of the strength or weakness of the anti-freeze.

12 Claims, 6 Drawing Figures

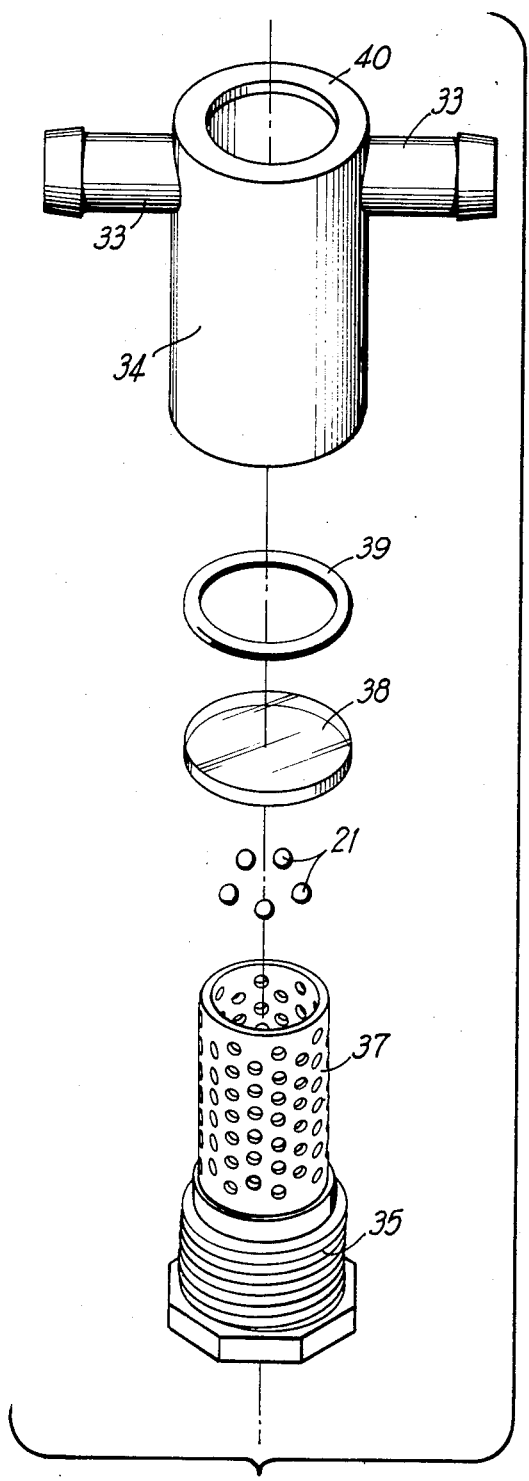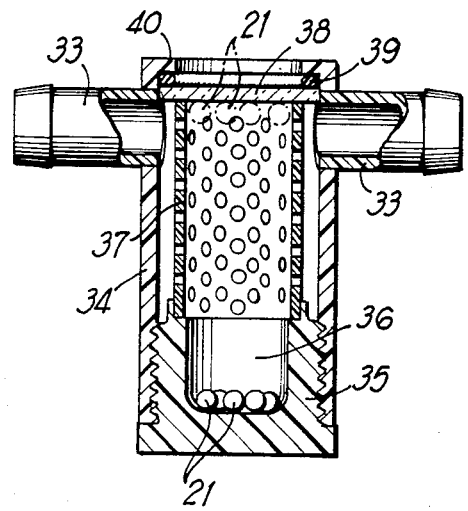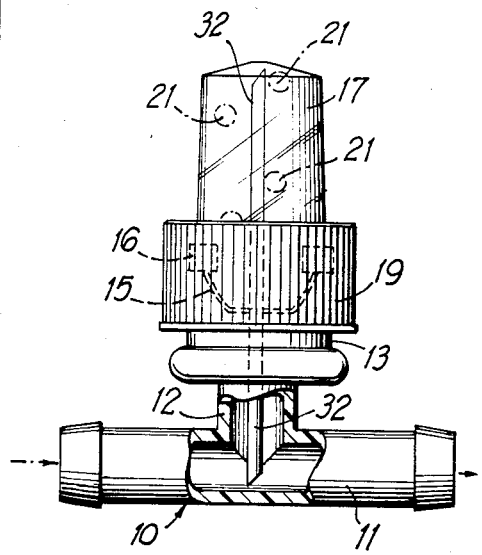

COOLANT LINE HYDROMETER

BACKGROUND OF THE INVENTION

The objective of the present invention is to provide a simplified and reliable hydrometer unit for permanent installation directly in an engine coolant line, such as an automobile heater hose, whereby a direct visual indication of anti-freeze strength or weakness in the liquid coolant is obtainable at any time without the necessity for manipulating or even touching the hydrometer unit.

A further object of the invention is to provide a coolant line hydrometer of inexpensive construction which utilizes specific gravity of the coolant to provide a direct visual indication of coolant strength or weakness. A plurality of variously colored float elements contained within a coolant receiving chamber of the hydrometer are individually formulated to float and position themselves adjacent to a transparent viewing portion of the hydrometer to indicate the condition or strength of the anti-freeze component of the coolant, based on its specific gravity at any given time. If no float elements are viewable, the anti-freeze strength is inadequate. If a single float element is viewable, the anti-freeze strength is somewhat greater but may still be inadequate. If two or more float elements are viewable, an increasing anti-freeze strength is visually indicated.

A further feature of the invention is that the coolant line hydrometer unit can be used to drain liquid coolant from the system and additional anti-freeze can be added to the system through the hydrometer unit. Also, the device can be employed with a garden hose to flush out the coolant system after opening the drain at the bottom of the engine radiator.

Other features and advantages of the invention will become apparent during the course of the following description.

BRIEF DESCRIPTION OF THE DRAWINGS

FIG. 4 is a further side elevation, partly in section, of the device according to FIG. 1 and showing another variant of the invention.

FIG. 5 is an exploded perspective view showing a further embodiment of the invention.

FIG. 6 is a vertical section taken through the assembled device shown in FIG. 5.

DETAILED DESCRIPTION

Figure 1:
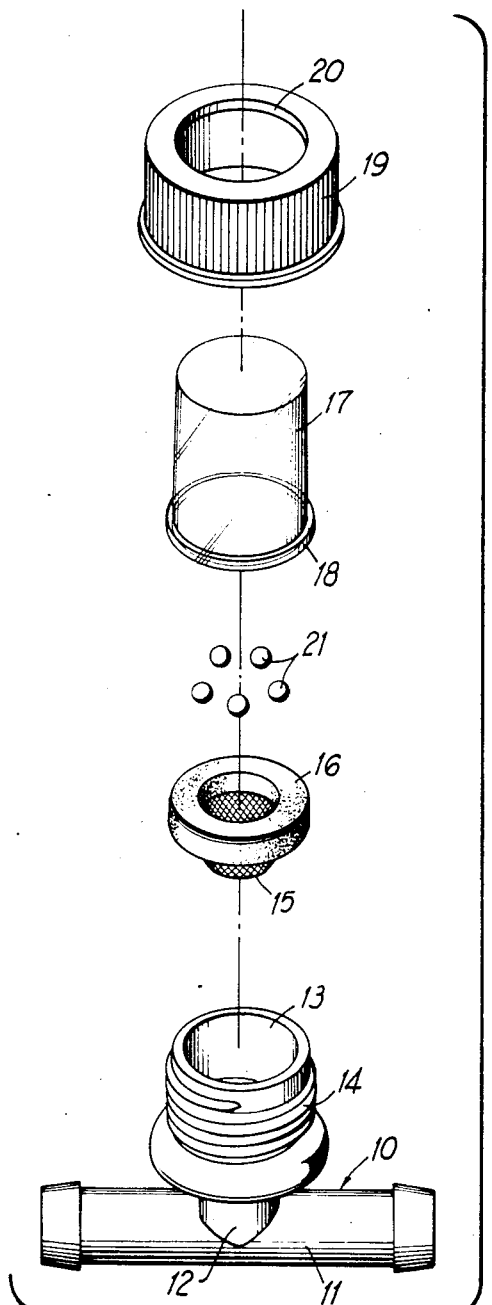
FIG. 1 is a perspective view of a coolant line hydrometer according to one embodiment of the present invention.
Figure 2:
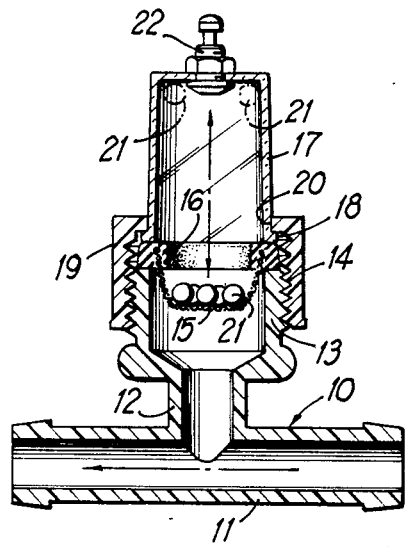
FIG. 2 is a vertical section taken through the assembled device shown in FIG. 1 and depicting a variant of the invention.

Referring to the drawings in detail wherein like numerals designate like parts, and referring first to FIGS. 1 and 2, a T-fitting 10 includes a main branch 11 adapted to be directly connected permanently in an engine coolant line, such as a heater hose of an automobile coolant system. The T-fitting includes a center lateral branch 12 which is positioned upright when the T-fitting is installed with suitable clamps, not shown, in a heater hose or the like. The short upright branch 12 carries an integral bowl 13 which is externally screw-threaded as at 14 and which is open at its top. A depressed screen element 15 having an upper end compressible gasket 16 is received within the chamber of the bowl 13, as shown in FIG. 2, with the gasket 16 resting on the top horizontal edge of the bowl 13.

A clear viewing dome 17 has a bottom flange 18 resting on the gasket 16 and being clamped thereagainst by an internally threaded cap 19 which engages the external threads 14 of the bowl 13. The cap 19 has a top opening 20 through which the viewing dome 17 extends upwardly for a considerable distance above the top of the cap 19.

A plurality of variously colored float balls 21, such as five float balls, is contained in the chamber defined by the viewing dome 17 and screen element 15. These colored float balls are individually formulated to float in the liquid coolant at different concentrations of an antifreeze constituent, such as ethylene glycol. As the anti-freeze concentration of the liquid coolant decreases over a period of time, the specific gravity of the coolant is diminished and the colored float balls designed to float at a greater anti-freeze concentration do not float, but remain seated on the screen element 15, as shown in FIG. 2. Those float balls which are formulated to float at lesser coolant specific gravities will float and rise within the viewing dome 17 as shown in broken lines in FIG. 2, to provide a direct visual indication of the strength of the anti-freeze in the coolant.

For example, if one colored ball, say a green ball, rises in the dome 17 to the viewing position, the liquid coolant may resist freezing to +20° F. If two balls 21, such as a green and red ball, rise in the dome 17, the coolant may resist freezing to +5° F. If three balls rise in the dome 17, such as green, red and white balls, the coolant may resist freezing to −10° F. If four balls, green, red, white and yellow, rise in the viewing dome 17, the coolant may resist freezing to −30° F. Finally, if five balls, green, red, white, yellow and blue, rise in the dome 17, the anti-freeze protection may be good down to −50° F.

It should be understood that the invention is not restricted to the use of any particular number of float balls 21, five such balls representing a preferred arrangement, nor is the invention restricted to the use of colored balls. Balls of a single color can be utilized, if desired, in which case the number of balls rising into the dome 17 will indicate the strength of the anti-freeze.

In the example previously given for five variously colored float balls 21, it will be understood that if no ball rises into the viewing dome 17 the anti-freeze strength is well below acceptable levels in colder climates.

FIG. 2 includes a variant of the invention comprising an air release valve 22 installed on the top wall of the dome 17, and serving to discharge any air which might be trapped in the top of the dome.

Figure 3:
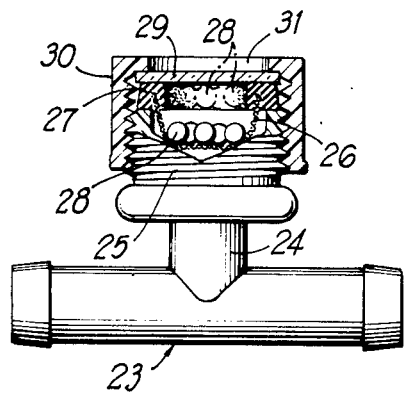
FIG. 3 is a side elevation, partly in section, showing a second embodiment of the invention.

FIG. 3 depicts a second embodiment of the invention comprising a T-fitting 23 adapted for connection more-or-less permanently in a coolant hose and having an upright extension 24 carrying an open top externally screw-threaded bowl 25 receiving therein a screen element 26 having an upper end gasket 27. A plurality of float elements 28 are provided, such as the previously described variously colored float balls.

In lieu of the clear viewing dome 17, a clear flat viewing disc or lens 29 is utilized and rests on the gasket 27, and is clamped in place by an internally threaded cap 30 which engages the threads of the bowl 25. The cap 30 has a top opening 31 adjacent to the lens 29. If the cap 30 is formed of transparent material and is provided with a transparent top wall, the lens 29 can be omitted and the floating indicator balls in the hydrometer can be viewed through the top wall of the cap as they float to indicating positions against or near such wall.

The general operation of the device according to FIG. 3 is the same as described for the first embodiment of the invention shown in FIGS. 1 and 2.

FIG. 4 shows another variant of the invention in FIGS. 1 and 2 in which the air release valve 22 is omitted and replaced by an internal vent tube 32 which places the top of the dome 17 in direct communication with the interior of the T-fitting branch 11. With this arrangement, any air tending to collect in the top of viewing dome 17 can pass through the vent tube 32 and enter the main coolant flow path through the T-fitting 10. All other parts of the device in FIG. 4 are identical to corresponding parts shown in FIGS. 1 and 2, and the basic mode of operation of the invention is exactly as described in connection with FIGS. 1 and 2.

FIGS. 5 and 6 show another embodiment of the invention which differs from all of the previous embodiments in that the chamber or reservoir containing the float balls is located below the coolant flow path rather than above it. This eliminates the need for the air release valve 22 or a vent tube 32.

In FIGS. 5 and 6, a tubular coolant fitting 33 is connected directly in a coolant hose or line. The fitting 33 carries a sleeve 34 which extends vertically below the fitting 33 and is internally threaded at its lower end portion to receive an externally threaded cap 35 defining a bowl chamber 36 adapted to contain the float balls 21. A perforated sleeve 37 extends from the upper end of the cap 35 and is interengaged therewith as shown in FIG. 6. A clear viewing lens 38 extends across and engages the top edge of the perforated sleeve 37 and an elastic ring seal 39 is placed between the lens and the top wall 40 of sleeve 34.

When the cap 35 is adequately tightened, the parts are held securely in assembled relationship. Liquid coolant flowing in the fitting 33 can descend into and fill the space surrounding and within the perforated sleeve 37 and also the bowl chamber 36. The indicator float balls 21 can float and rise through the sleeve 37 and place themselves against the lens 38 to provide a visual indication of anti-freeze concentration in the same manner described previously for the preceding embodiments of the invention. As stated, the construction according to FIGS. 5 and 6 has the advantage of eliminating possible trapping of air in the top of the hydrometer. All embodiments of the invention, however, provide a permanently installed coolant line direct reading hydrometer which requires no mechanical manipulation in order to get an accurate visual indication of anti-freeze strength at any time this is desired.

Coolant can be drained from the system through the hydrometer assembly as by removing the dome 17 and cap 19 and fresh anti-freeze can be added to the system through the hydrometer. Similarly, the system can be flushed by attaching a garden hose to the threads 14 after removal of the cap 19 and by opening the drain near the bottom of the radiator.

It is to be understood that the forms of the invention herewith shown and described are to be taken as preferred examples of the same, and that various changes in the shape, size and arrangement of parts may be resorted to, without departing from the spirit of the invention or scope of the subjoined claims.

We claim:

1. A hydrometer unit for connection in an automobile coolant flow line comprising: a t-shaped fitting adapted to be connected to said coolant flow line; a coolant receiving chamber means connected to said t-shaped fitting for receiving coolant from the t-shaped fitting; and indicating float elements contained within the coolant receiving chamber means and adapted to rise therein individually as a function of the specific gravity of the coolant; said coolant receiving chamber means including a closure cap which when connected to said t-shaped fitting forms a coolant receiving chamber, retaining means for retaining said indicating float elements within said coolant receiving chamber, a viewing window member of a substantially clear material through which said float elements can be visually observed the coolant receiving chamber means, and air venturi means located within said coolant receiving chamber means for automatically removing air which may collect within said coolant chamber means.

2. A hydrometer unit as defined in claim 1, and the viewing window member comprising a substantially clear viewing dome rising above said closure cap.

3. A hydrometer unit as defined in claim 2, and a trapped air release valve on the top of said clear viewing dome.

4. A hydrometer unit as defined in claim 1, and said viewing window member comprising a substantially flat viewing lens disposed near the top face of said closure cap.

5. A hydrometer unit as defined in claim 1, and said indicating float elements comprising individually formulated float balls each adapted to rise in a liquid coolant of a certain specific gravity individual to one of the float balls.

6. A hydrometer unit as defined in claim 5, and each float ball having a color differing from the colors of the other float balls.

7. A hydrometer unit as defined in claim 1, and said coolant receiving chamber means comprising a chamber means on and communicating with said tubular fitting and extending substantially below the coolant flow path defined by the fitting, and said viewing window means comprising a substantially clear viewing lens near the top of the chamber means and near said fitting.

8. A hydrometer unit as defined in claim 7, and the coolant receiving chamber means comprising a sleeve attached to said fitting substantially at right angles thereto, and a perforated sleeve within said sleeve in spaced substantially concentric relationship therewith and extending between said closure cap and viewing lens and across said fitting.

9. A hydrometer unit as defined in claim 8, and a ring seal disposed between the top face of the viewing lens and an opposing end wall of said sleeve.

10. A hydrometer unit for connection in a coolant flow line comprising:
a tubular fitting adapted to be connected to a coolant flow line;
a coolant receiving chamber means connected to said tubular fitting for receiving coolant from the fitting, said coolant receiving chamber means including a bowl element rising vertically above said tubular fitting, a porous seat mounted on said bowl element, a viewing window member on and above said seat and bowl element, and a retainer cap for said viewing window member and said porous seat engaged with said bowl element, the viewing window member comprising a substantially clear viewing dome rising above said retainer cap;

indicating float elements contained within the coolant receiving chamber means and adapted to rise therein individually as a function of the specific gravity of the coolant;

and an air vent tube within said coolant receiving chamber means extending from the top of said dome downwardly to the interior of said tubular fitting.

11. A hydrometer unit for connection in an automobile coolant flow line comprising: a tubular fitting adapted to be connected to said coolant flow line; a coolant receiving chamber means connected to said tubular fitting for receiving coolant from the tubular fitting; and indicating float elements contained within the coolant receiving chamber means and adapted to rise therein individually as a function of the specific gravity of the coolant; said coolant receiving chamber means including a closure cap which when connected to said tubular fitting forms a coolant receiving chamber, retaining means for retaining said indicating float elements within said coolant receiving chamber, a viewing window member of a substantially clear material through which said float elements can be visually observed within the coolant receiving chamber means, and air venturi means located within said coolant receiving chamber means for automatically removing air which may collect within said coolant chamber means.

12. A hydrometer unit as defined in claim 11 in which said tubular fitting is T-shaped.

* * * * *